United States Patent [19]

Deemer

[11] 4,340,364
[45] Jul. 20, 1982

[54] ENDODONTIC TEST FILE

[76] Inventor: Milton G. Deemer, 3982 Hackberry Pl., Castro Valley, Calif. 94546

[21] Appl. No.: 179,052

[22] Filed: Aug. 18, 1980

[51] Int. Cl.³ .......................... A61C 3/00; A61C 5/02
[52] U.S. Cl. ..................................... 433/75; 433/72; 433/102
[58] Field of Search ........................... 433/75, 72, 102

[56] References Cited

U.S. PATENT DOCUMENTS

| | | | |
|---|---|---|---|
| 639,359 | 11/1899 | Schultz | 433/102 |
| 1,067,015 | 7/1913 | Fowler | 433/102 |
| 1,366,877 | 1/1921 | Craig | 433/75 |
| 3,772,791 | 11/1973 | Malmin | 433/75 |
| 3,935,640 | 2/1976 | Cohen | 433/75 |
| 4,190,958 | 3/1980 | Martin et al. | 433/102 |
| 4,231,738 | 11/1980 | Riitano et al. | 433/102 |

FOREIGN PATENT DOCUMENTS

| | | | |
|---|---|---|---|
| 929867 | 6/1955 | Fed. Rep. of Germany | 433/102 |
| 2404997 | 8/1975 | Fed. Rep. of Germany | 433/102 |
| 290446 | 8/1953 | Sweden | 433/102 |

Primary Examiner—Gene Mancene
Assistant Examiner—John J. Wilson
Attorney, Agent, or Firm—Linval B. Castle

[57] ABSTRACT

An endodontic test file for use in root canal therapy for quickly and accurately measuring the length between the crown occlusal surface and the apex of the root canal without the necessity of x-rays. The test file has a smooth tapered shank with calibrations etched along the shank, a convenient handle on the larger end of the shank and at the narrow end, a sharp screw tip having a total screw length of only approximately 0.5 mm. In operation the test file is inserted into the previously prepared coronal cavity and is screwed through the root canal until rotation of the screw tip no longer advances the test file through the canal. At this point, the tip has passed through the apex and into the infected soft periodontal ligament. The etched shaft calibrations then indicate the precise tooth length.

3 Claims, 2 Drawing Figures

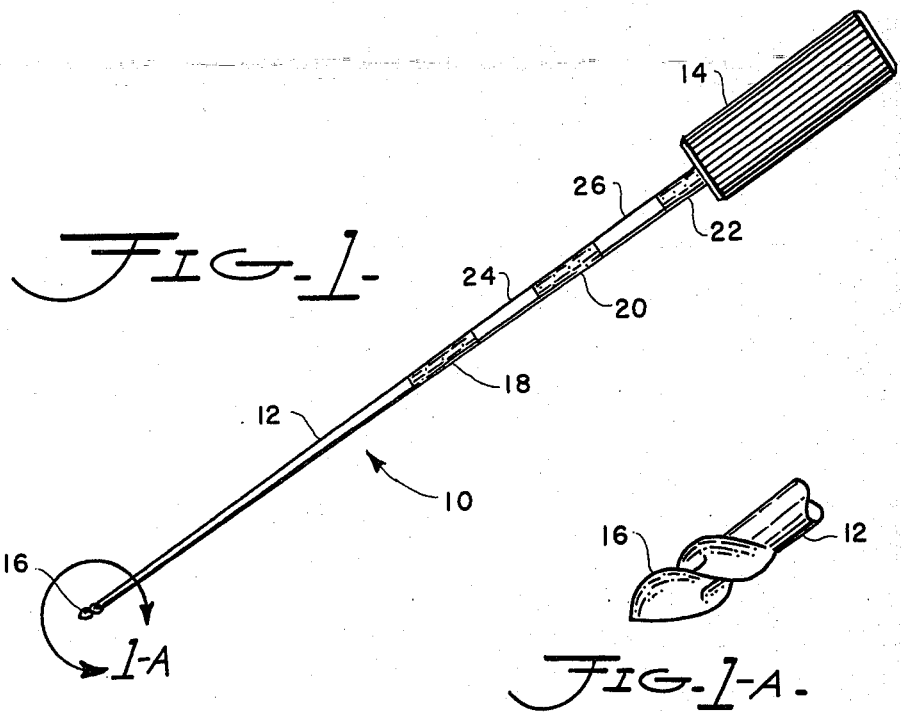
FIG_1.
FIG_1-A.
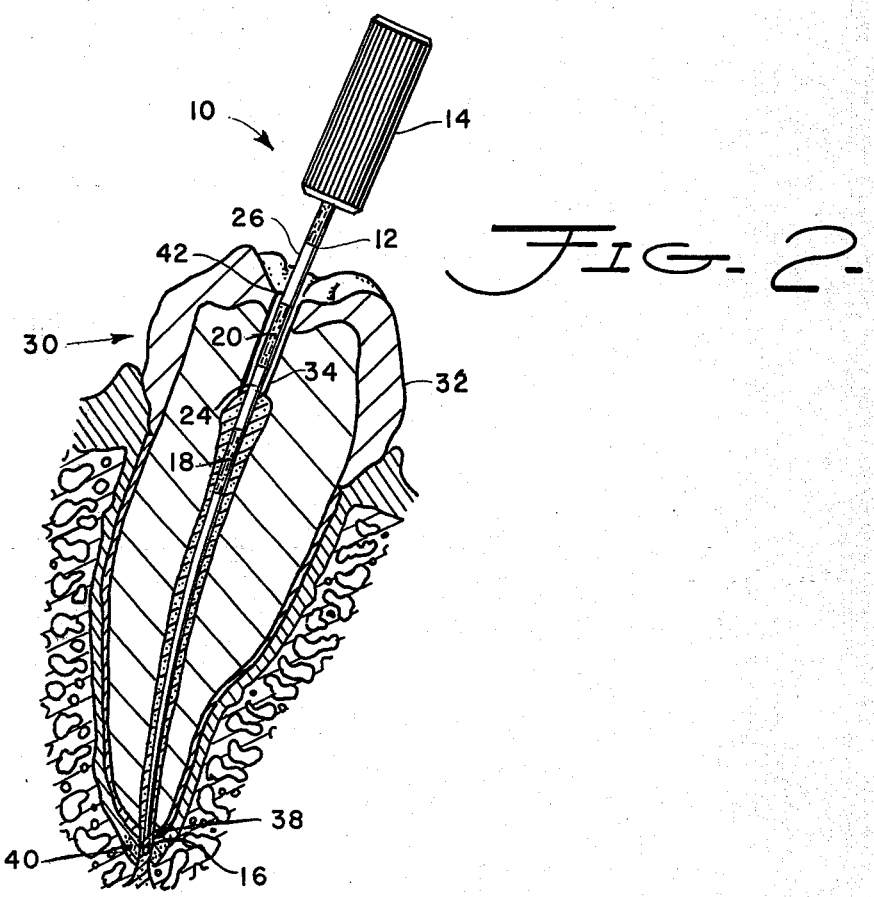
FIG_2.

ENDODONTIC TEST FILE

BRIEF SUMMARY OF THE INVENTION

This invention relates generally to dental instruments and particularly to an endodontic test file for quickly and accurately measuring the total length of a tooth.

In root canal therapy, the accurate determination of tooth length is critical. Such determination will establish the apical extent of instrumentation within the canal and the ultimate level of the root canal filling. In accurate determination of tooth length may lead to inadequate or excessive canal debridement that may result in acute post-operative pain, prolonged healing periods, or a complete failure of the root canal therapy because of incomplete regeneration of the cementum, the periodontal ligament and/or the alveolar bone.

Heretofore the accepted method of accurate determination of tooth length involved the steps of measuring the tooth on the preoperative x-ray film, subtracting 2 mm or 3 mm as a safety allowance and set the stop to that length on an endodontic file, placing the instrument in the canal up to the stop, and taking a second x-ray with the file in position. The film of the second x-ray is then measured to determine the length between the end of the file and the point where the canal leaves the root and the file stop is readjusted to this length less approximately 0.5 mm as a safety allowance. Because of the possibility of x-ray distortion and measuring error, a third or confirmatory x-ray is often taken at this point and the stop on the file is readjusted as necessary to the precise length of the tooth. Using files and reamers adjusted to this precise length, the dental surgeon can then clean the entire canal to the apex in preparation for subsequent filling.

Since this prior art method requires the extensive use of x-rays and the adjustment and readjustment of the stop mechanism on the file or probe used for determining the precise tooth length, even the most skilled and experienced dental surgeon will require a minimum of 10 to 20 minutes to make a tooth length determination.

The endodontic test file of the invention provides a very rapid and accurate means for measuring the tooth length without necessity of stop adjustments and confirmatory x-rays during the process. Thus, a procedure which formerly required 10 to 20 minutes may, by the use of the test file, be reduced to approximately 15 seconds. It is apparent that this reduced period will materially reduce the tensions on the surgeon and the patient and will, in addition, not expose the patient to possible excessive x-ray radiation.

Briefly described, the test file of the invention comprises a smooth tapered shank of conventional file lengths of approximately 21 mm to 30 mm with calibration bands etched every 2 mm or 3 mm along the shank. A convenient endodontic file handle is attached at the larger diameter end of the shank and a sharp screw having a length of only ½ mm to 1 mm is at the narrow end of the shank. The screw diameter is larger than the diameter of the narrow end of the shank so that when the test file is screwed through a root canal, the screw tip engages the dentin of the canal walls to be drawn further through the canal until it automatically disengages when the tip emerges from the root apex and into the soft infected periodontal ligament. The number of etched calibration bands extending from a predetermined reference on the coronal surface may then be observed to determine the total length of the tooth between that reference and the root apex. The screw tip is then backed out of the root canal and stops on endodontic files and reamers that may then be adjusted to the precise length necessary to continue the root canal therapy.

DESCRIPTION OF THE DRAWINGS

In the drawings which illustrate a preferred embodiment of the invention;

FIG. 1 is a drawing illustrating the endodontic test file;

FIG. 1A is an enlarged view of the sharp screw tip of the test file of FIG. 1; and FIG. 2 is a cross-section drawing of a typical premolar and the use of the test file of FIG. 1 for determining the length of the tooth.

DETAILED DESCRIPTION OF THE PREFERRED EMBODIMENT

Illustrated in FIG. 1 is an endodontic test file 10 in accordance with the invention. Test file 10 includes a strong, resilient, smooth, tapered shank 12 with a convenient handle 14 at the larger diameter end, and a sharp screw tip 16 at the narrower end. The shank 10 may be of any convenient length and preferably has a length similar to conventional endodontic files that range in length between approximately 21 mm and 30 mm. In the preferred embodiment, the taper of the shank 12 is somewhat greater than that employed in the test file and may, for example, have a diameter of 0.5 mm at the narrow end adjacent the screw tip 16 and increased to approximately 1.5 mm at the end adjacent the handle 14. This increased taper is desirable to provide additional strength to the shank 12 and thereby reduce the possibility of breakage during use.

Beginning approximately 16 mm from the end of shank 12 that joins the screw tip 16, is a series of etched bands 18, 20, 22 which preferably have a length along the shank 12 of 3 mm and are spaced from each other by polished or unetched bands 24 and 26 that have a similar length of 3 mm. When the test file 10 is in use and inserted into the root canal, the dental surgeon may accurately determine the tooth length by observing the quantity and amount of the band extending from the crown of the tooth, as will be subsequently explained.

The sharp screw tip 16 at the narrow end of shank 12 preferably has a length of between 0.5 mm and 1.0 mm and has an overall diameter slightly larger (e.g., 0.2 mm) than the narrowest diameter of the shank 12, as best illustrated in FIG. 1A. The screw tip 16 may have any convenient thread or point configuration as long as the tip can effectively screw into the soft dentin of the root and draw the shank 12 deeper into the canal.

The use of test file 10 is illustrated in FIG. 2 within the root canal of a premolar tooth 30. As illustrated, the tooth crown 32 has been opened to expose the root canal 34. The endodontic test file 10 has then been inserted into the root canal and the handle 14 rotated so that the screw tip 16 passes through the canal and through the apex 38 of the root. As the tip 16 leaves the apex 38 and enters the soft infected periodontal ligament 40, the screw tip 16 no longer has any firm material into which it can screw and further rotation of the handle 14 will not draw the test file 10 any further through the canal 34.

Having located the bottom or apex 38 of the root, the dental surgeon may now examine the calibration bands etched on the shank 12. If the first calibration band 18 begins at the conventional 16 mm from the end of the shank 12, i.e., the junction of the shank 12 and the tip 16, and if each of the calibration bands has a length of 3 mm, it can readily be observed that the portion of the calibration band 26 extending above the coronal cavity 42 is extremely close to 2.5 mm. The test file is therefore inserted through the root canal by a distance of 25.5 mm and this is the total length of the tooth 30.

After the measurement has been made, the handle 14 is rotated in the opposite direction to screw the tip 16 from the ligament 40 and out through the root canal. The dental surgeon, knowing the precise length between the coronal cavity 42 and apex 38 may then accurately adjust the stop mechanisms on the files and reamers to be used for the subsequent canal debridement with assurance that the instruments will reach the apex without further penetration.

Having thus described the invention, what is claimed is:

1. An endodontic test file for measuring the length of tooth between the apex of its root and the crown, said test file comprising:
   a smooth, strong, tapered, resilient, shank having a total length substantially greater than the estimated length of the tooth and a small diameter end smaller than that of the root canal of said tooth;
   a handle connected to the large diameter end of said shank for manually rotating said shank;
   a screw tip attached to said small diameter end of said shank, said tip having sharpened screw threads, said threads having a maximum diameter greater than the diameter of said small diameter end of said shank and a maximum length of approximately 1 mm, whereby rotation of said tip will draw said shank through said root canal to a point where said tip passes through the apex of said root canal; and
   measuring means marked on said shank for indicating distances along said shank between said screw tip and said handle, the indicated marking at the level of the tooth crown representing the length of the tooth between said apex and said crown.

2. The endodontic test file claimed in claim 1 wherein said measuring means comprises calibration bands etched on said shaft, said bands having a predetermined width and being spaced from each other along said shaft by said same predetermined width.

3. The endodontic test file claimed in claim 2 wherein said predetermined width is 3 mm, and the first of said bands begins at a distance of 16 mm from said screw tip.

* * * * *